United States Patent [19]
Armentano et al.

[11] Patent Number: 5,824,544
[45] Date of Patent: Oct. 20, 1998

[54] ADENOVIRUS VECTORS FOR GENE THERAPY

[75] Inventors: Donna Armentano, Belmont; Helen Romanczuk, Westboro; Samuel Charles Wadsworth, Shrewsbury, all of Mass.

[73] Assignee: Genzyme Corporation, Framingham, Mass.

[ * ] Notice: The term of this patent shall not extend beyond the expiration date of Pat. No. 5,707,618.

[21] Appl. No.: 540,077

[22] Filed: Oct. 6, 1995

Related U.S. Application Data

[63] Continuation-in-part of Ser. No. 409,874, Mar. 24, 1995.

[51] Int. Cl.$^6$ .................................................. C12N 15/00
[52] U.S. Cl. ...................... 435/320.1; 514/44; 435/172.3
[58] Field of Search ............................. 435/320.1, 235.1, 435/252.3, 240.1; 514/44, 2

[56] References Cited

FOREIGN PATENT DOCUMENTS

| W9412649 | 12/1993 | WIPO . |
|---|---|---|
| 9424297 | 10/1994 | WIPO . |
| 9428152 | 12/1994 | WIPO . |
| 9502697 | 1/1995 | WIPO . |
| WO9511984 | 5/1995 | WIPO . |

OTHER PUBLICATIONS

Zabner et al., Gene Therapy 3:458–465, 1996.
Armentano et al., Human Gene Therapy 6:1343–1353, 1995.
Krougliak et al., Human Gene Therapy 6:1575–1586, 1995.
Welsh et al., Human Gene Therapy 6:205–218, 1995.
Wadsworth et al., J. Cell Biochem. Supp. 21A, Abtstract No. C6–450, 1995.
Setoguchi et al., Blood 84:2946–2953, 1994.
Engelhardt et al., Human Gene Therapy 5:1217–1229, 1994.
Armentano et al., J. Cell Biochem. Supp. 18A, Abstract No. DZ 102, 1994.
Wilkinson et al., Nucleic Acids Res. 20:2233–2239, 1992.
Rosenfeld et al., Cell 68:145–155, 1992.
Jolly, D., Cancer Gene Therapy 1:51–64, 1994.
Hodgson, C.P., BioTechnology 13:222–225, 1995.
Horwitz, M.S., "Adenoviridae and Their Replication," in Virology, 2nd edition, Fields, B.N., et al., eds., Raven Press, New York, 1990.
Berkner, K.L., Curr. Top. Micro. Immunol. 158:39–66, 1992.
Graham, F.L., J. Gen. Virol. 36:59–72, 1977.
Vincent et al., Nature Genetics 5:130–134, 1993.
Descamps et al., Human Gene Therapy 5:979–985, 1994.
Stratford–Perricaudet et al., Human Gene Therapy 1:241–256, 1990.
Mitani et al., Human Gene Therapy 5:941–948, 1994.
Haddada et al., Human Gene Therapy 4:703–711, 1993.
Jaffe et al., Nature Genetics 1:372–378, 1992.
Zabner, J. et al., Nature Genetics 6:75–83, 1994.
Rich, D. et al., Human Gene Therapy 4:461–476, 1993.
Zabner, J. et al., Cell 75:207–216, 1993.
Crystal, R.G. et al., Nature Genetics 8:42–51, 1994.
Bridge, E. et al., J. Virol. 63:631–638, 1989.
Huang, M. et al., J. Virol. 63:2605–2615, 1989.
Klessig, D. et al., Mol. Cell. Biol. 4:1354–1362, 1984.
Weinberg, D. et al., Proc. Natl. Acad. Sci. USA 80:5383–5386, 1983.
Ghosh–Choudhury et al., J. EMBO 6:1733–1739, 1987.
Hehir et al., Pediatr. Pulmon., Supp. 12, 1995, Abstract.
Marshall, Science, 269, 1995, 1050–1055.
Miller, FASEB J., 9, 1995, 190–199.
Culver et al., Trends in Genetics, 10(5), 1994, 174–178.
Hodgson, Exp. Opin. Ther. Pat., 5(5), 1995, 458–469.
Neve, Trends Neuroscience, 16(7), 1993, 251–253.
Berkner, BioTechniques, 6(7), 1988, 616–629.
Wills et al., Human Gene Therapy, 5, 1994, 1079–1088.

Primary Examiner—Jasemine C. Chambers
Assistant Examiner—Deborah J. R. Clark
Attorney, Agent, or Firm—Baker & Botts, LLP

[57] ABSTRACT

The present invention relates to novel adenovirus vectors for use in gene therapy which are designed to prevent the generation of replication-competent adenovirus (RCA) during in vitro propagation and clinical use. The invention also provides methods for the production of the novel virus vectors. These vectors maximize safety for clinical applications in which adenovirus vectors are used to transfer genes into recipient cells for gene therapy.

6 Claims, 10 Drawing Sheets

E.C. = expression cassette containing transgene of interest

|  | 5 | 10 | 15 | 20 | 25 | 30 | 35 | Kb |
|---|---|---|---|---|---|---|---|---|
| Ad2 | | | | | | | | 35937 |
| Ad2/CFTR-1 | | | | | | | | 37532 |
| CFTR-1 RCA | | | | | | | | |
| Ad2/CFTR-2 | | | | | | | | 36351 |
| CFTR-2 RCA | | | | | | | | |
| Ad2/CFTR-3 | | | | | | | | 35966 |
| CFTR-3 RCA | | | | | | | | |
| Ad2/CFTR-5 | | | | | | | | 36277 |
| CFTR-5 RCA | | | | | | | | |
| Ad2/CFTR-6 | | | | | | | | 36133 |
| CFTR-6 RCA | | | | | | | | |
| Ad2/CFTR-7 | | | | | | | | 33832 |
| CFTR-7 RCA | | | | | | | | |
| Ad2/CFTR-8 | | | | | | | | 36117 |
| CFTR-8 RCA | | | | | | | | |
| Ad5 | | | | | | | | 36935 |

FIG. 5

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 600 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
CATCATCAAT  AATATACCTT  ATTTTGGATT  GAAGCCAATA  TGATAATGAG  GGGGTGGAGT     60
TTGTGACGTG  GCGCGGGGCG  TGGGAACGGG  GCGGGTGACG  TAGTAGTGTG  GCGGAAGTGT    120
GATGTTGCAA  GTGTGGCGGA  ACACATGTAA  GCGCCGGATG  TGGTAAAAGT  GACGTTTTTG    180
GTGTGCGCCG  GTGTATACGG  GAAGTGACAA  TTTTCGCGCG  GTTTTAGGCG  GATGTTGTAG    240
TAAATTTGGG  CGTAACCAAG  TAATATTTGG  CCATTTTCGC  GGGAAAACTG  AATAAGAGGA    300
AGTGAAATCT  GAATAATTCT  GTGTTACTCA  TAGCGCGTAA  TATTTGTCTA  GGGCCGCGGG    360
GACTTTGACC  GTTTACGTGG  AGACTCGCCC  AGGTGTTTTT  CTCAGGTGTT  TTCCGCGTTC    420
CGGGTCAAAG  TTGGCGTTTT  ATTATTATAG  TCAGCTGACG  CGCAGTGTAT  TTATACCCGG    480
TGAGTTCCTC  AAGAGGCCAC  TCTTGAGTGC  CAGCGAGTAG  AGTTTTCTCC  TCCGAGCCGC    540
TCCGACACCG  GGACTGAAAA  TGAGACATAT  TATCTGCCAC  GGAGGTGTTA  TTACCGAAGA    600
```

( 2 ) INFORMATION FOR SEQ ID NO:2:

( i ) SEQUENCE CHARACTERISTICS:
        ( A ) LENGTH: 1796 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

```
CATAACATGG  TGTGTGGCAA  CTGCGAGGAC  AGGGCCTCTC  AGATGCTGAC  CTGCTCGGAC     60
GGCAACTGTC  ACTTGCTGAA  GACCATTCAC  GTAGCCAGCC  ACTCTCGCAA  GGCCTGGCCA    120
GTGTTTGAGC  ACAACATACT  GACCCGCTGT  TCCTTGCATT  TGGGTAACAG  GAGGGGGGTG    180
TTCCTACCTT  ACCAATGCAA  TTTGAGTCAC  ACTAAGATAT  TGCTTGAGCC  CGAGAGCATG    240
TCCAAGGTGA  ACCTGAACGG  GGTGTTTGAC  ATGACCATGA  AGATCTGGAA  GGTGCTGAGG    300
TACGATGAGA  CCCGCACCAG  GTGCAGACCC  TGCGAGTGTG  GCGGTAAACA  TATTAGGAAC    360
```

| | | | | | |
|---|---|---|---|---|---|
| CAGCCTGTGA | TGCTGGATGT | GACCGAGGAG | CTGAGGCCCG | ATCACTTGGT | GCTGGCCTGC | 420
| ACCCGCGCTG | AGTTTGGCTC | TAGCGATGAA | GATACAGATT | GAGGTACTGA | AATGTGTGGG | 480
| CGTGGCTTAA | GGGTGGGAAA | GAATATATAA | GGTGGGGGTC | TCATGTAGTT | TTGTATCTGT | 540
| TTTGCAGCAG | CCGCCGCCAT | GAGCGCCAAC | TCGTTTGATG | GAAGCATTGT | GAGCTCATAT | 600
| TTGACAACGC | GCATGCCCCC | ATGGGCGGG | GTGCGTCAGA | ATGTGATGGG | CTCCAGCATT | 660
| GATGGTCGCC | CCGTCCTGCC | CGCAAACTCT | ACTACCTTGA | CCTACGAGAC | CGTGTCTGGA | 720
| ACGCCGTTGG | AGACTGCAGC | CTCCGCCGCC | GCTTCAGCCG | CTGCAGCCAC | CGCCCGCGGG | 780
| ATTGTGACTG | ACTTTGCTTT | CCTGAGCCCG | CTTGCAAGCA | GTGCAGCTTC | CCGTTCATCC | 840
| GCCCGCGATG | ACAAGTTGAC | GGCTCTTTTG | GCACAATTGG | ATTCTTTGAC | CCGGGAACTT | 900
| AATGTCGTTT | CTCAGCAGCT | GTTGGATCTG | CGCCAGCAGG | TTTCTGCCCT | GAAGGCTTCC | 960
| TCCCCTCCCA | ATGCGGTTTA | AAACATAAAT | AAAAACCAGA | CTCTGTTTGG | ATTTTGATCA | 1020
| AGCAAGTGTC | TTGCTGTCTT | TATTTAGGGG | TTTTGCGCGC | GCGGTAGGCC | CGGGACCAGC | 1080
| GGTCTCGGTC | GTTGAGGGTC | CTGTGTATTT | TTTCCAGGAC | GTGGTAAAGG | TGACTCTGGA | 1140
| TGTTCAGATA | CATGGGCATA | AGCCCGTCTC | TGGGGTGGAG | GTAGCACCAC | TGCAGAGCTT | 1200
| CATGCTGCGG | GGTGGTGTTG | TAGATGATCC | AGTCGTAGCA | GGAGCGCTGG | GCGTGGTGCC | 1260
| TAAAAATGTC | TTTCAGTAGC | AAGCTGATTG | CCAGGGGCAG | GCCCTTGGTG | TAAGTGTTTA | 1320
| CAAAGCGGTT | AAGCTGGGAT | GGGTGCATAC | GTGGGGATAT | GAGATGCATC | TTGGACTGTA | 1380
| TTTTTAGGTT | GGCTATGTTC | CCAGCCATAT | CCCTCCGGGG | ATTCATGTTG | TGCAGAACCA | 1440
| CCAGCACAGT | GTATCCGGTG | CACTTGGGAA | ATTTGTCATG | TAGCTTAGAA | GGAAATGCGT | 1500
| GGAAGAACTT | GGAGACGCCC | TTGTGACCTC | CGAGATTTTC | CATGCATTCG | TCCATATATT | 1560
| TCTGGGATCA | CTAACGTCAT | AGTTGTGTTC | CAGGATGAGA | TCGTCAATGA | TGGCAATGGG | 1620
| CCCACGGGCG | GCGGCCTGGG | CGAAGATAGG | CCATTTTTAC | AAAGCGCGGG | CGGAGGGTGC | 1680
| CAGACTGCGG | TATAATGGTT | CCATCCGGCC | CAGGGGCGTA | GTTACCCTCA | CAGATTTGCA | 1740
| TTTCCCACGC | TTTGAGTTCA | GATGGGGGGA | TCATGTCTAC | CTGCGGGGCG | ATGAAG | 1796

( 2 ) INFORMATION FOR SEQ ID NO:3:

( i ) SEQUENCE CHARACTERISTICS:
  ( A ) LENGTH: 600 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

| | | | | | |
|---|---|---|---|---|---|
| CATCATCAAT | AATATACCTT | ATTTGGATT | GAAGCCAATA | TGATAATGAG | GGGTGGAGT | 60
| TTGTGACGTG | GCGCGGGGCG | TGGGAACGGG | GCGGGTGACG | TAGTAGTGTG | GCGGAAGTGT | 120
| GATGTTGCAA | GTGTGGCGGA | ACACATGTAA | GCGACGGATG | TGGCAAAAGT | GACGTTTTG | 180
| GTGTGCGCCG | GTGTACACAG | GAAGTGACAA | TTTTCGCGCG | GTTTAGGCG | GATGTTGTAG | 240
| TAAATTTGGG | CGTAACCGAG | TAAGATTTGG | CCATTTTCGC | GGGAAAACTG | AATAAGAGGA | 300

-continued

| | | | | | |
|---|---|---|---|---|---|
| AGTGAAATCT | GAATAATTTT | GTGTTACTCA | TAGCGCGTAA | TATTTGTCTA | GGGCCGCGGG | 360 |
| GACTTTGACC | GTTTACGTGG | AGACTCGCCC | AGGTGTTTTT | CTCAGGTGTT | TTCCGCGTTC | 420 |
| CGGGTCAAAG | TTGGCGTTTT | ATTATTATAG | TCAGCTGACG | TGTAGTGTAT | TTATACCCGG | 480 |
| TGAGTTCCTC | AAGAGGCCAC | TCTTGAGTGC | CAGCGAGTAG | AGTTTTCTCC | TCCGAGCCGC | 540 |
| TCCGACACCG | GGACTGAAAA | TGAGACATAT | TATCTGCCAC | GGAGGTGTTA | TTACCGAAGA | 600 |

( 2 ) INFORMATION FOR SEQ ID NO:4:

( i ) SEQUENCE CHARACTERISTICS:
        ( A ) LENGTH: 1800 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

| | | | | | |
|---|---|---|---|---|---|
| CATAACATGG | TATGTGGCAA | CTGCGAGGAC | AGGGCCTCTC | AGATGCTGAC | CTGCTCGGAC | 60 |
| GGCAACTGTC | ACCTGCTGAA | GACCATTCAC | GTAGCCAGCC | ACTCTCGCAA | GGCCTGGCCA | 120 |
| GTGTTTGAGC | ATAACATACT | GACCCGCTGT | TCCTTGCATT | TGGGTAACAG | GAGGGGGGTG | 180 |
| TTCCTACCTT | ACCAATGCAA | TTTGAGTCAC | ACTAAGATAT | TGCTTGAGCC | CGAGAGCATG | 240 |
| TCCAAGGTGA | ACCTGAACGG | GGTGTTTGAC | ATGACCATGA | AGATCTGGAA | GGTGCTGAGG | 300 |
| TACGATGAGA | CCCGCACCAG | GTGCAGACCC | TGCGAGTGTG | GCGGTAAACA | TATTAGGAAC | 360 |
| CAGCCTGTGA | TGCTGGATGT | GACCGAGGAG | CTGAGGCCCG | ATCACTTGGT | GCTGGCCTGC | 420 |
| ACCCGCGCTG | AGTTTGGCTC | TAGCGATGAA | GATACAGATT | GAGGTACTGA | AATGTGTGGG | 480 |
| CGTGGCTTAA | GGGTGGGAAA | GAATATATAA | GGTGGGGGTC | TTATGTAGTT | TTGTATCTGT | 540 |
| TTTGCAGCAG | CCGCCGCCGC | CATGAGCACC | AACTCGTTTG | ATGGAAGCAT | TGTGAGCTCA | 600 |
| TATTTGACAA | CGCGCATGCC | CCCATGGGCC | GGGGTGCGTC | AGAATGTGAT | GGGCTCCAGC | 660 |
| ATTGATGGTC | GCCCCGTCCT | GCCCGCAAAC | TCTACTACCT | TGACCTACGA | GACCGTGTCT | 720 |
| GGAACGCCGT | TGGAGACTGC | AGCCTCCGCC | GCCGCTTCAG | CCGCTGCAGC | CACCGCCCGC | 780 |
| GGGATTGTGA | CTGACTTTGC | TTTCCTGAGC | CCGCTTGCAA | GCAGTGCAGC | TTCCCGTTCA | 840 |
| TCCGCCCGCG | ATGACAAGTT | GACGGCTCTT | TTGGCACAAT | GGATTCTTT | GACCCGGGAA | 900 |
| CTTAATGTCG | TTTCTCAGCA | GCTGTTGGAT | CTGCGCCAGC | AGGTTTCTGC | CCTGAAGGCT | 960 |
| TCCTCCCCTC | CCAATGCGGT | TTAAAACATA | AATAAAAAAC | CAGACTCTGT | TTGGATTTGG | 1020 |
| ATCAAGCAAG | TGTCTTGCTG | TCTTTATTTA | GGGGTTTTGC | GCGCGCGGTA | GGCCCGGGAC | 1080 |
| CAGCGGTCTC | GGTCGTTGAG | GGTCCTGTGT | ATTTTTTCCA | GGACGTGGTA | AAGGTGACTC | 1140 |
| TGGATGTTCA | GATACATGGG | CATAAGCCCG | TCTCTGGGGT | GGAGGTAGCA | CCACTGCAGA | 1200 |
| GCTTCATGCT | GCGGGGTGGT | GTTGTAGATG | ATCCAGTCGT | AGCAGGAGCG | CTGGGCGTGG | 1260 |
| TGCCTAAAAA | TGTCTTTCAG | TAGCAAGCTG | ATTGCCAGGG | GCAGGCCCTT | GGTGTAAGTG | 1320 |
| TTTACAAAGC | GGTTAAGCTG | GGATGGGTGC | ATACGTGGGG | ATATGAGATG | CATCTTGGAC | 1380 |
| TGTATTTTTA | GGTTGGCTAT | GTTCCCAGCC | ATATCCCTCC | GGGGATTCAT | GTTGTGCAGA | 1440 |
| ACCACCAGCA | CAGTGTATCC | GGTGCACTTG | GGAAATTTGT | CATGTAGCTT | AGAAGGAAAT | 1500 |

```
GCGTGGAAGA  ACTTGGAGAC  GCCCTTGTGA  CCTCCAAGAT  TTTCCATGCA  TTCGTCCATA  1560
ATGATGGCAA  TGGGCCCACG  GGCGGCGGCC  TGGGCGAAGA  TATTTCTGGG  ATCACTAACG  1620
TCATAGTTGT  GTTCCAGGAT  GAGATCGTCA  TAGGCCATTT  TTACAAAGCG  CGGGCGGAGG  1680
GTGCCAGACT  GCGGTATAAT  GGTTCCATCC  GGCCCAGGGG  CGTAGTTACC  CTCACAGATT  1740
TGCATTTCCC  ACGCTTTGAG  TTCAGATGGG  GGGATCATGT  CTACCTGCGG  GGCGATGAAG  1800
```

ADENOVIRUS VECTORS FOR GENE THERAPY

SPECIFICATION

The present application is a continuation-in-part of application Ser. No. 08/409,874 filed Mar. 24, 1995.

The present invention relates to novel adenovirus vectors for use in gene therapy which are designed to prevent the generation of replication-competent adenovirus (RCA) during in vitro propagation and clinical use. The invention also provides methods for the production of the novel virus vectors. These vectors maximize safety for clinical applications in which adenovirus vectors are used to transfer genes into recipient cells for gene therapy.

BACKGROUND OF THE INVENTION

Prospects for gene therapy to correct genetic disease or to deliver therapeutic molecules depend on the development of gene transfer vehicles that can safely deliver exogenous nucleic acid to a recipient cell. To date, most efforts have focused on the use of virus-derived vectors that carry a heterologous gene (transgene) in order to exploit the natural ability of a virus to deliver genomic content to a target cell.

Most attempts to use viral vectors for gene therapy have relied on retrovirus vectors, chiefly because of their ability to integrate into the cellular genome. However, the disadvantages of retroviral vectors are becoming increasingly clear, including their tropism for dividing cells only, the possibility of insertional mutagenesis upon integration into the cell genome, decreased expression of the transgene over time, rapid inactivation by serum complement, and the possibility of generation of replication-competent retroviruses (Jolly, D., *Cancer Gene Therapy* 1:51–64, 1994; Hodgson, C.P., *Bio Technology*13:222–225, 1995).

Adenovirus is a nuclear DNA virus with a genome of about 36 kb, which has been well-characterized through studies in classical genetics and molecular biology (Horwitz, M. S., "Adenoviridae and Their Replication," in Virology, 2nd edition, Fields, B. N., et al., eds., Raven Press, New York, 1990). The genome is classified into early (known as E1–E4) and late (known as L1–L5) transcriptional units, referring to the generation of two temporal classes of viral proteins. The demarcation between these events is viral DNA replication.

Adenovirus-based vectors offer several unique advantages, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39–66, 1992; Jolly, D., *Cancer Gene Therapy* 1:51–64, 1994). The cloning capacity of an adenovirus vector is about 8 kb, resulting from the deletion of certain regions of the virus genome dispensable for virus growth, e.g., E3, deletions of regions whose function is restored in trans from a packaging cell line, e.g., E1, and its complementation by 293 cells (Graham, F. L., *J. Gen. Virol.* 36:59–72, 1977), as well as the upper limit for optimal packaging which is about 105%–108% of wild-type length.

Genes that have been expressed to date by adenoviral vectors include p53 (Wills et al., *Human Gene Therapy* 5:1079–188, 1994); dystrophin (Vincent et al., *Nature Genetics* 5:130–134, 1993; erythropoietin (Descamps et al., *Human Gene Therapy* 5:979–985, 1994; ornithine transcarbamylase (Stratford-Perricaudet et al., *Human Gene Therapy* 1:241–256, 1990); adenosine deaminase (Mitani et al., *Human Gene Therapy* 5:941–948, 1994); interleukin-2 (Haddada et al., *Human Gene Therapy* 4:703–711, 1993); and α1-antitrypsin (Jaffe et al., *Nature Genetics* 1:372–378, 1992).

The tropism of adenoviruses for cells of the respiratory tract has particular relevance to the use of adenovirus in gene therapy for cystic fibrosis (CF), which is the most common autosomal recessive disease in Caucasians, that causes pulmonary dysfunction because of mutations in the transmembrane conductance regulator (CFTR) gene that disturb the cAMP-regulated C_channel in airway epithelia (Zabner, J. et al., *Nature Genetics* 6:75–83, 1994). Adenovirus vectors engineered to carry the CFTR gene have been developed (Rich, D. et al., *Human Gene Therapy* 4:461–476, 1993) and studies have shown the ability of these vectors to deliver CFTR to nasal epithelia of CF patients (Zabner, J. et al., *Cell* 75:207–216, 1993), the airway epithelia of cotton rats and primates (Zabner, J. et al., *Nature Genetics* 6:75–83, 1994), and the respiratory epithelium of CF patients (Crystal, R. G. et al., *Nature Genetics* 8:42–51, 1994).

One of the critical issues remaining in the development of safe viral vectors is to prevent the generation of replication-competent virus during vector production in a packaging cell line or during gene therapy treatment of an individual. The generation of these replication competent viruses poses the threat of an unintended virus infection with attendant pathological consequences for the patient.

The presence of wild-type adenovirus in the recipient cells of human candidates for gene therapy presents a possibility for generating replication-competent adenovirus (RCA) due to homologous DNA sequences present in the vector and the recipient cells (Jolly, D., *Cancer Gene Therapy* 1:51–64, 1994). Furthermore, the generation of new viruses carrying a transgene may interfere with dosage requirements for optimal gene therapy as extra copies of the gene may be produced by new viruses carrying the transgene. It is therefore critical to develop vectors that are not only replication-defective, but are designed to minimize recombinogenic potential as well limit the harmful effects of a recombination event by self-destruction.

SUMMARY OF THE INVENTION

This invention provides for gene therapy vectors that are effective to deliver useful genes to patients and which are constructed to minimize toxic or immunologic consequences to the patient.

The invention is directed to novel adenovirus vectors which are inactivated by the occurrence of a recombination event within a packaging cell or a recipient cell and therefore prevent the generation of replication-competent adenovirus (RCA). The inactivation may occur through the loss of an essential gene, or by the generation of a vector genome that cannot be packaged.

The invention is also directed to vectors which minimize the occurrence of a recombination event with packaging cells or recipient cells by vector genome rearrangements that decrease homology with viral sequences that may be present in a packaging cell or a recipient cell in order to prevent the generation of RCA.

These vector designs increase the safety of recombinant adenovirus vectors for use as gene transfer vehicles in gene therapy applications.

Thus, in one aspect, the invention provides a nucleotide sequence which contains elements of an adenovirus genome as well as a heterologous gene of mammalian origin that is under the control of a eucaryotic transcriptional promoter.

This nucleotide sequence is capable of functioning as a vector which allows expression of the aforementioned heterologous gene when the vector is placed in a cell of an individual. The said nucleotide sequence is further characterized by the absence from the sequence of a first element of the adenovirus genome that is essential to replication or packaging of the adenovirus in a host mammalian cell and the placement of a second element of the adenovirus genome that is itself essential to the replication or packaging of adenovirus in a host mammalian cell into the nucleotide sequence at, or directly adjacent to, the location the nucleotide sequence otherwise occupied by the first element.

An additional aspect of the invention is a nucleotide sequence where the first element is the E1a–E1b region of adenovirus genome and the second element may be any one of the E4 region of adenovirus, the region E2A, the gene encoding terminal protein or adenovirus structural proteins, such as fiber L5.

A still further aspect provides a nucleotide sequence containing elements of an adenovirus genome and a heterologous gene of mammalian origin that is under the control of a eucaryotic transcriptional promoter, in which the E1a–E1b region of the adenovirus genome is absent and where a stuffer sequence has been inserted into the nucleotide sequence in a location other than that of the heterologous gene of mammalian origin. A vector containing this sequence is further characterized in that legitimate recombination of the sequence with an element that is present in a helper cell used to replicate or package the sequence, or with an element that is present in a cell of an individual, and having homology with the Ea–E1b region, leads to the production of a lengthened nucleotide sequence that is substantially less efficient than an unmodified nucleotide sequence at being packaged in the helper cell or in a cell of said individual.

The invention also provides for a nucleotide sequence, as above, that includes the gene for adenoviral protein IX and a heterologous gene of mammalian origin that is under the control of a eucaryotic transcriptional promoter. This latter nucleotide sequence is characterized in that the E1a–E1b region of the adenovirus genome is absent and the gene that encodes protein IX has been repositioned to a location that deviates from its normal location in the wild-type adenovirus genome.

The invention further provides for a nucleotide sequence, as above, that deletes the gene for adenoviral protein IX and includes a heterologous gene of mammalian origin that is under the control of a eucaryotic transcriptional promoter. This nucleotide sequence is also characterized in that the E1a–E1b region of the adenovirus genome is absent, and that the sequence does not exceed about 90% of the length of the adenovirus genome.

The invention also provides for a method for minimizing exposure of an individual undergoing gene therapy, using a virus vector to deliver a heterologous gene, to replication-competent virus comprising the step of treating said individual with a gene therapy composition that itself comprises a pharmaceutically acceptable carrier, and one or another of the vectors having the nucleotide sequences described above.

BRIEF DESCRIPTION OF THE FIGURES

FIG. 5 BclI restriction enzyme analysis of wild-type adenovirus serotypes 2 and 5 and of the adenovirus vectors shown in FIG. 4. The restriction enzyme pattern of RCA generated during vector production in 293 cells is shown below each vector.

Figure 1:
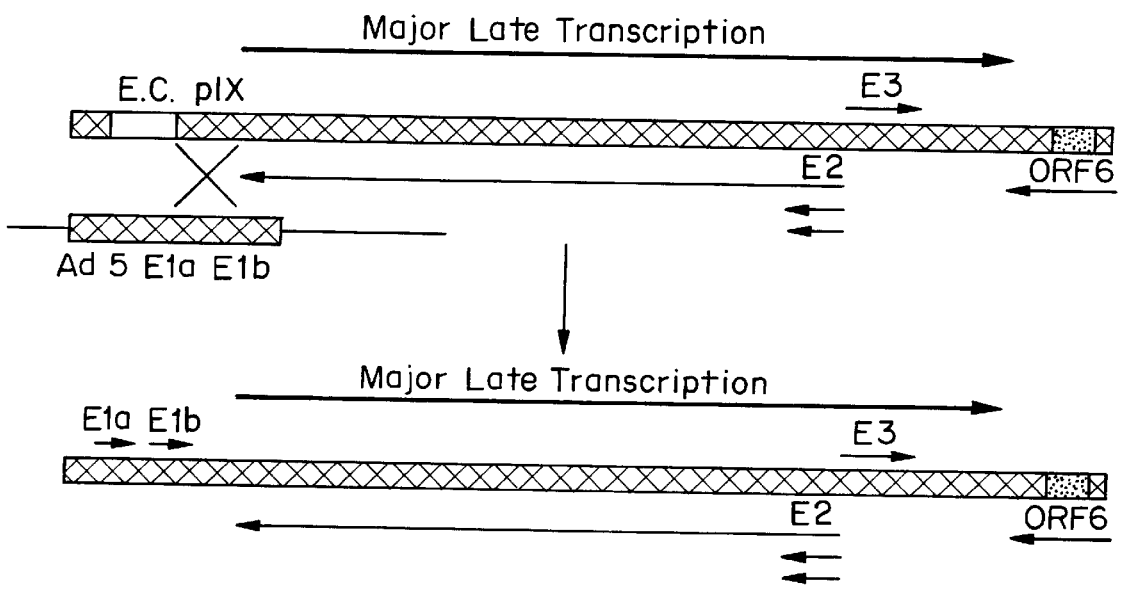
FIG. 1 Schematic diagram of current vector constructs, and the depiction of a recombination event in 293 cells. New constructs are depicted that produce a replication-incompetent vector by the deletion of an essential gene following recombination.
Figure 1:
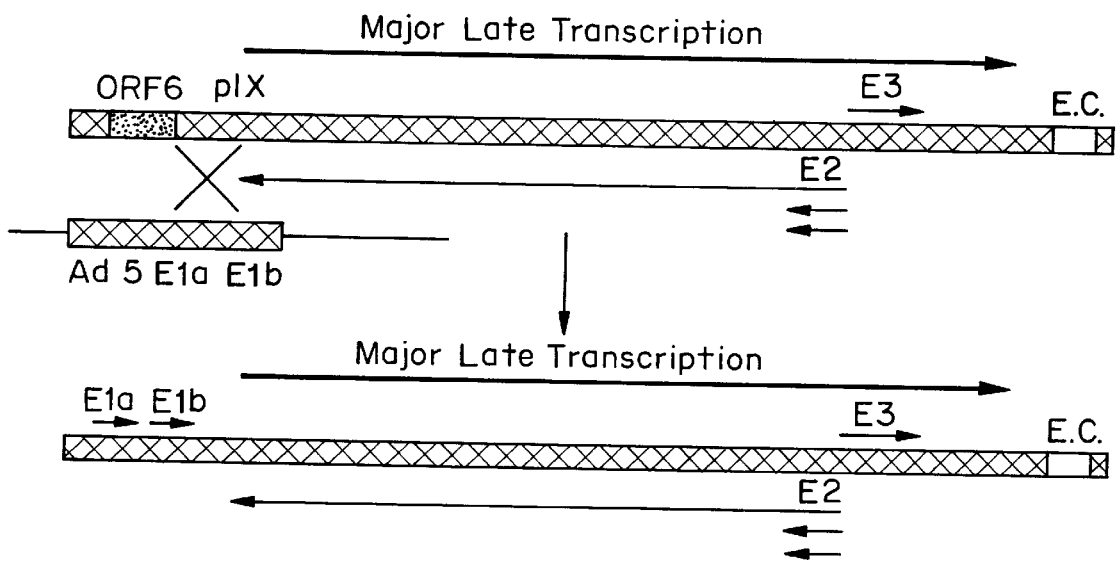

The infective dose used in the RCA assay is shown where E=exponent, and is expressed in infectious units (IU).

DETAILED DESCRIPTION OF THE INVENTION

The invention is directed to adenovirus vectors which are inactivated by the occurrence of a legitimate recombination event within a packaging cell or a recipient cell and therefore prevent the generation of replication-competent adenovirus (RCA). Legitimate recombination is that which is dependent on specific and normal base pairing at sequences recognized as having homology for each other. The inactivation may occur through the loss of an essential gene, or by the generation of a vector genome that cannot be packaged.

The invention is also directed to vectors which minimize the occurrence of a recombination event with packaging cells or recipient cells by vector genome rearrangements that decrease homology with viral sequences that may be present in a packaging cell or a recipient cell to prevent the generation of RCA. Recipient cells targeted for gene therapy may contain wild-type adenovirus DNA sequence that can recombine with an adenovirus vector (Jolly, D., *Cancer Gene Therapy* 1:51–64, 1994).

These vector designs therefore increase the safety of recombinant adenovirus vectors for use as gene transfer vehicles in gene therapy applications.

Thus, in one aspect, the invention provides a nucleotide sequence which contains elements of an adenovirus genome as well as a heterologous gene of mammalian origin that is under the control of a eucaryotic transcriptional promoter. This nucleotide sequence is capable of functioning as a vector which allows expression of the aforementioned heterologous gene when the vector is placed in a cell of an individual. The nucleotide sequence is further characterized by the absence from the sequence of a first element of the adenovirus genome that is essential to replication or packaging of the adenovirus in a host mammalian cell and the placement of a second element of the adenovirus genome that is itself essential to the replication or packaging of adenovirus in a host mammalian cell into the nucleotide sequence at, or directly adjacent to, the location the nucleotide sequence otherwise occupied by the first element.

It is understood according to the practice of the invention that the reference to elements of the viral genome (such as first and second elements, referred to herein) that are termed essential includes also reference to elements that facilitate replication or packaging but which are not absolutely essential to such processes.

With respect to this aspect of the invention, the heterologous gene is any gene which is recognized as useful. Representative examples include genes of mammalian origin encoding, for example, proteins or useful RNAs; viral proteins such as herpes thymidine kinase, and bacterial cholera toxin for cytotoxic therapy.

An additional aspect of the invention is a nucleotide sequence where the first element is the E1a–E1b region of adenovirus genome and the second element may be any one of the E4 region of adenovirus, the region E2A, the gene encoding terminal protein or adenovirus structural proteins, such as fiber L5.

A still further aspect provides a nucleotide sequence containing elements of an adenovirus genome and a heterologous gene of mammalian origin that is under the control of a eucaryotic transcriptional promoter, in which the E1a–E1b region of the adenovirus genome is absent and where a stuffer sequence has been inserted into the nucleotide sequence in a location other than that of the heterologous gene of mammalian origin. A vector containing this sequence is further characterized in that legitimate recombination of the sequence with an element that is present in a helper cell used to replicate or package the sequence, or with an element that is present in a cell of an individual, and having homology with the E1a–E1b region, leads to the production of a lengthened nucleotide sequence that is substantially less efficient than an unmodified nucleotide sequence at being packaged in the helper cell or in a cell of said individual.

By additional sequence it is meant an inert sequence which does not affect adversely the function of the vector. The length of the additional sequence is selected based on the length of the sequence deleted. For example, if the deletion consists of the E1 region, an acceptable insert is about 3 kb, which is based on principles known by those skilled in the art, based on consideration of vector length for optimal packaging.

The invention also provides for a nucleotide sequence, as above, that includes the gene for adenoviral protein IX and a heterologous gene of mammalian origin that is under the control of a eucaryotic transcriptional promoter. This latter nucleotide sequence is characterized in that the E1a–E1b region of the adenovirus genome is absent and the gene that encodes protein IX has been repositioned to a location that deviates from its normal location in the wild-type adenovirus genome.

Preferably, it is repositioned to a location of generally at least about 100 nucleotides removed, preferably about 500 nucleotides removed, and most preferably, about 100 nucleotides removed.

The invention also provides for a nucleotide sequence, as above, that deletes the gene for adenoviral protein IX and includes a heterologous gene of mammalian origin that is under the control of a eucaryotic transcriptional promoter. This nucleotide sequence is also characterized in that the E1a–E1b region of the adenovirus genome is absent, and that the sequence does not exceed about 90% of the length of the adenovirus genome.

The invention also provides for a method for minimizing exposure of an individual undergoing gene therapy, using a virus vector to deliver a heterologous gene, to replication-competent virus comprising the step of treating said individual with a gene therapy composition that itself comprises a pharmaceutically acceptable carrier, and vectors using the nucleotide sequences described above.

Recombination-Dependent

Target Sequence Deletion Vectors

This aspect of the invention relates to vectors that prevent the generation of RCA by an adenovirus vector design in which an essential gene or genomic segment (the deletion target) is placed within a region that is potentially subject to recombination because a packaging cell or recipient cell contains homologous viral sequences. The result of a potential recombination event between cellular sequences and the vector is that this essential gene or genomic segment is deleted upon recombination, thereby rendering the viral vector replication-incompetent. This is accomplished by rearranging the genome so that the deletion target is moved from its original genomic location to be located within the region potentially subject to recombination. Although recombination may restore a missing viral sequence, the virus will be impaired by the loss of an essential gene that is caused by the recombination event.

In one embodiment of the invention, this vector design is applicable to preventing recombination events in a p ackaging cell line, such as 293 cells (Graham, F. L., *J. Gen. Virol.* 36:59–72, 1977). These cells, which contain an intact contiguous viral E1 DNA sequence derived from adenovirus 5 from the 5' ITR to about nucleotide 4300 (ref. for numbering is Roberts, R. J., in *Adenovirus DNA*, Oberfler, W., ed., Matinus Nihoft Publishing, Boston, 1986) integrated into the genome, a re able to supply the E1 gene products in trans to an E1-deleted adenovirus vector. The generation of RCA is possible from recombination between the E1 sequences in the cell and the remaining sequences at the boundary of E1 in the vector, such as protein IX, if enough flanking homologous sequence is present to facilitate a legitimate recombination event.

In a specific embodiment, an adenovirus vector deleted for the E1 region and the E4 region except for the ORF6 gene is constructed by inserting an expression cassette into the E4-deleted region. (FIG. 1). The ORF6 gene is moved to the E1-deleted region. The E4 region of an adenovirus vector may be deleted except for ORF6 due to its role in DNA replication, late mRNA accumulation, and shutoff of host protein synthesis (Bridge, E. et al.,*J. Virol.* 63:631–638, 1989; Huang, M. et al., *J. Virol.* 63:2605–2615, 1989. If a recombination event occurs between the viral sequences and 293 cells, the E1 sequences are gained and the ORF6 gene is deleted, such that the vector is still replication-defective.

In a further aspect of the invention, a vector may be customized to prevent the generation of RCA from any packaging cell line. The deletion target gene or segment will be engineered into the region of the vector which has homology with the DNA contained in the packaging cell line. Thus, recombination within this region will cause the target gene or segment to be deleted, resulting in the generation of replication-incompetent viral vectors. Vectors in which the deletion target is inserted into the E2 or E4 regions, for example, may be designed to circumvent recombination events in packaging cell lines that supply E2 or E4 gene products (Klessig, D. et al., *Mol. Cell. Biol.* 4:1354–1362, 1984; Weinberg, D. et al., *PNAS* 80:5383–5386, 1983). Analogous constructs designed to circumvent recombination in analogous packaging cell lines are within the scope of the invention.

In a further embodiment of this invention, this vector design can be used to preclude the formation of RCA from recombination with wild-type adenovirus that may be present in a patient's cell. The presence of wild-type adenovirus in human candidates for adenovirus-based gene therapy may present a source of viral DNA sequences for recombination events that generate RCA from a replication-incompetent adenovirus vector (Jolly, D., *Cancer Gene Therapy* 1:51–64, 1994). Prevention of RCA production may be accomplished by placing essential genes or segments within one or more regions in the vector that may potentially be subject to recombination with the wild-type adenovirus. By placing essential targets in potential sites for recombination, one or more recombination events will serve to delete essential viral genes, and thereby render the viral vector replication-incompetent.

Figure 2:
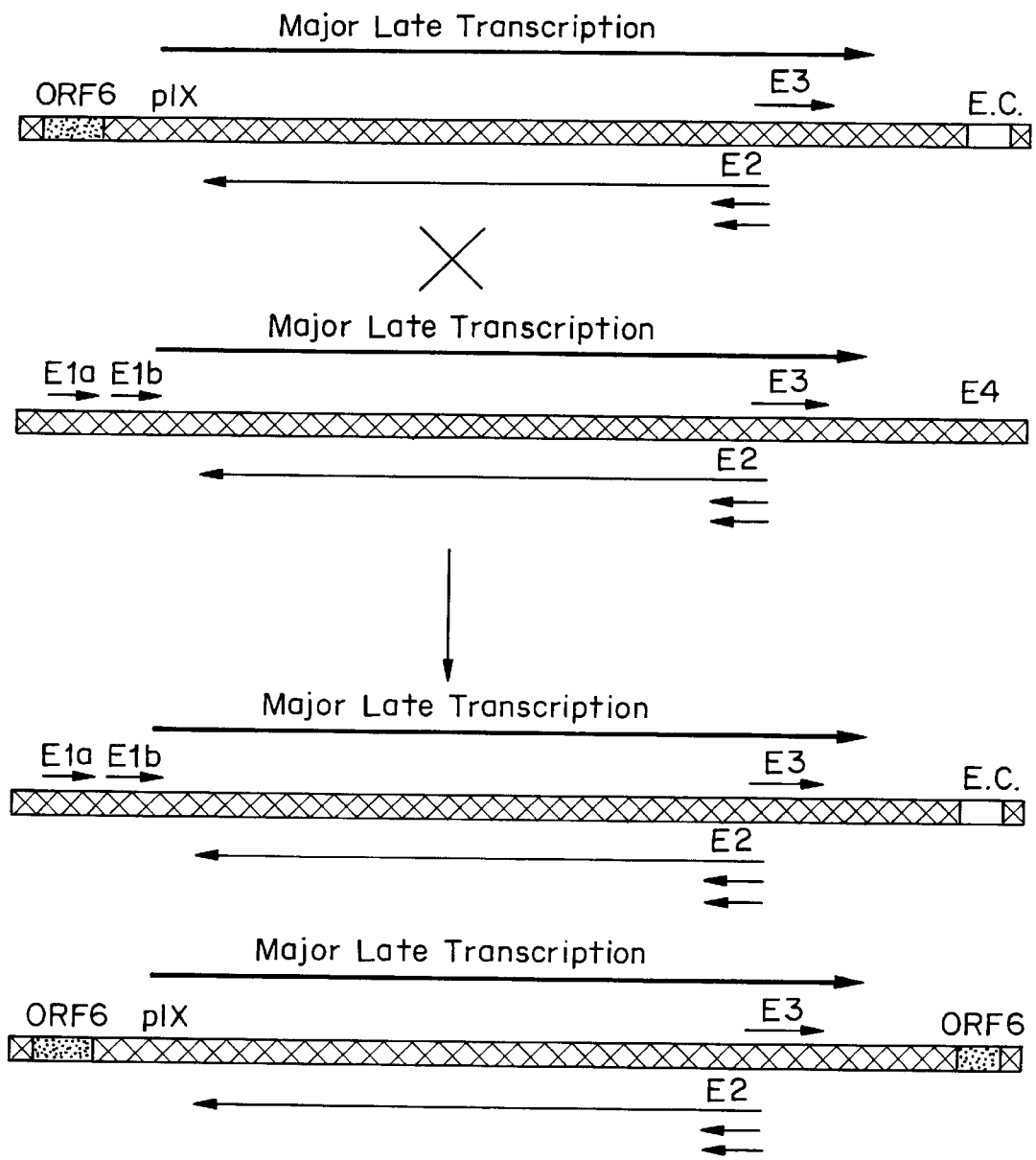
FIG. 2 A novel vector of the invention is depicted which, upon recombination with wild-type virus, produces replication-incompetent vectors deleted for an essential gene or segment.

In another embodiment, depicted in FIG. 2, a vector is constructed that upon recombination with wild-type virus, is rendered replication-incompetent. The vector contains the ORF6 gene positioned in the deleted E1 region, and an expression cassette inserted into the deleted E4 region. The central portion of the vector genome is homologous to wild-type adenovirus, and upon a recombination event, the vectors genomes so generated will be replication-incompetent as depicted in FIG. 2.

Essential adenovirus genes or genomic segments which may be positioned to serve as targets for deletion upon a recombination event include ORF6, L5 (fiber protein), the entire E4 region, the E2A region, terminal protein, or any other essential viral genes or segments.

Recombination-Dependent

Packaging-Defective Vectors

This aspect of the invention relates to vectors that are rendered packaging-defective upon the occurrence of a recombination event with a packaging cell or a recipient cell, preventing the generation of RCA. This design takes advantage of limitations that exist on the genome length that can be packaged into an adenovirus virion. The size of an adenovirus genome that can be optimally packaged into new virions may exceed its wild-type length up to about 105%–108% and still be packaged into new virions (Berkner, K. L., *Curr. Top. Micro. Immunol.* 158:39–66, 1992). If a recombination event generates a virus genome that exceeds the packaging limit, it will not be packaged and RCA are not generated.

Vectors that are packaging-defective following recombination can be created by engineering the vector DNA such that its length is at least 101% of the wild-type length. This can be accomplished even with vectors that contain deletions of the wild-type adenoviral genome because of the insertion of a heterologous DNA sequence that compensates for the deletion and maintains the genome at near-wild-type length.

The heterologous DNA sequence may solely code for a gene of interest, or alternatively, where a heterologous gene is at small size, additional heterologous stuffer DNA sequence may be added so as to render the vector genome at a size of at least 101% of wild-type length. Stuffer is a term generally recognized in the art intended to define functionally inert sequence intended to extend the length, thereof, such as certain portions of bacteriophage lambda.

In another embodiment of this aspect of the invention, a vector is designed in which the E1 region is deleted as well as the E4 region except for the ORF6 gene, for a total deletion of 5 kb, and the CFTR gene is inserted into the E4 deletion region. This vector size is 101.3% of wild-type length. Following an E1-mediated recombination event in 293 cells, for example, that inserts the E1 region into the vector, the genome will increase to about 108% of wild-type length, rendering it packaging-defective and preventing the generation of RCA.

It will be understood by those skilled in the art that the concept of recombination-dependent packaging-defective adenovirus vectors may be practiced by using any number of viral or non-viral DNA fragments that are engineered into any number of sites in the vector, with an overall goal of maintaining a vector size that will exceed optimal packaging length upon recombination.

Scrambled Genome Vectors That Minimize Recombination And

Generation Of RCA By Recombination

In this aspect of the invention, the vector genome derived from wild-type adenovirus is rearranged so as to perturb the linear arrangement of the viral coding regions. In one embodiment, this "scrambling" of the genome reduces the potential for recombination between a wild-type adenovirus that may be found in a human candidate for gene therapy and the adenovirus vector. This reduction is due to the fact that long stretches of homologous DNA sequences between the cell and vector are eliminated when the viral sequences in the vector are rearranged. The likelihood of recombination is reduced as the homologous regions are reduced in length. In this manner, the generation of RCA is minimized. Regions of the adenovirus genome which may be scrambled included, for example, the E2A region, the E4 region, ORF6, L5 (fiber protein), terminal protein, or any combination of these and other regions of the viral genome which result in a scrambled genome whose linear sequence deviates from wild-type.

This concept may be applied to vectors where more than one region of the adenovirus is deleted, such that restoration of replication-competence requires several recombination events, each of which is rendered less likely as the linear homology between the vector and cell is reduced by scrambling.

This concept may be analogously applied to minimizing recombination between an adenovirus vector and a packaging cell line, by designing the vector so that stretches of homology with the cell line are perturbed by rearrangement, reducing their effective length and the likelihood of recombination. In one example of this embodiment of the invention, the potential for recombination between an adenovirus vector and 293 cells is decreased by rearranging the protein IX sequences in the vector. The protein IX sequences are often found at the right-hand boundary of the deleted E1 region in a vector. Protein IX sequences are also contained within 293 cells at the boundary of the E1 adenovirus insert, and may facilitate recombination between the vector and cellular sequences. The result is that restoration of E1 sequences to the vector may occur by a protein IX-mediated recombination event. The relocation or mutagenesis of a protein IX boundary from the E1 deletion region in a vector will decrease the likelihood of such an event, and of the generation of RCA. Such a vector is described in Example 1, infra, and FIG. 3.

Ad2/CFTR-8 is particular embodiment of this aspect of the invention, and is shown in FIG. 5.

Prevention Of RCA With Vectors
Deleted For Homology With Packaging Cell Lines

This aspect of the invention relates to vector designs that prevent the generation of RCA during vector production by deletion of recombinogenic DNA sequences. RCA generation may occur during vector production when regions of homology exist between the viral DNA sequences in a replication-incompetent deletion vector and the viral DNA sequences in a packaging cell line that supplies viral proteins in trans. The vectors in this embodiment of the invention are designed such that regions of homology between the viral genome and the packaging cell line are further minimized by the deletion of non-essential viral DNA. These vectors are pared down to minimal viral sequences required to accomplish the goal of transporting a gene of interest into the target cell and presenting the gene to the cell for expression, but designed so that maximal safety is accomplished by preventing RCA formation.

Adenovirus DNA sequences that have been deleted in vector designs to date include sequences from the E1, E3 and E4 regions of the viral genome (Berkner, K. L., Curr. Top. Micro. Immunol. 158:39–66, 1992). The present invention provides vectors in which the protein IX region of the viral genome has been deleted so as to further reduce any homology with a packaging cell line containing adenovirus sequences. This deletion is particularly useful when vectors are being packaged in a cell line that includes protein IX sequences in the viral insert in the cell genome. For example, the 293 cell line widely used in adenovirus vector production contains the E1 regions and the protein IX sequence derived from adenovirus serotype 5 (Graham, F. L., J. Gen. Virol. 36:59–72, 1977), and is permissive for the growth of E1-deletion vectors.

A particular vector of the present invention, Ad2/CFTR-7, was constructed so as to delete the viral gene encoding protein IX. This gene is found at the right hand boundary of the E1B region and encodes a protein which is involved in packaging of full-length genomes during virion assembly (Ghosh-Choudhury, G. et al., J. EMBO 6:1733–1739, 1987). The protein IX DNA sequence in a vector has the potential for recombination with protein IX sequences contained within the adenovirus E1 insert in the 293 cell line. Because such a recombination event may generate RCA during the course of vector production, the vector described here provides a means to avoid this possibility by the removal of the protein IX recombinogenic sequences.

The removal of the protein IX gene is tolerated by a vector design that reduces the amount of DNA to be packaged, since protein IX is required to package genomes which are at least 90% of wild-type length (Ghosh-Choudhury, G. et al., J. EMBO 6:1733–1938, 1987). This may be accomplished by deletions of nonessential sequences, or by the deletion of sequences which are not necessary in cis, and whose gene products may be supplied in trans. Such sequences include those derived from the adenovirus El, E3 and E4 regions of the genome. In Ad2/CFTR-7, the E3 region was reduced in order to reduce genome length. It may be desirable to reduce the viral genome size with E3 deletions, yet retain some E3 sequences due to the fact that E3 proteins are involved in minimizing host immune response to adenovirus proteins (Horwitz, M. S., Adenoviridae and their Replication, in *Virology*, 2nd. ed., Fields, B. N. et al., eds., Raven Press, New York, 1990). In this manner, untoward consequences of viral vector introduction into a patient may be prevented.

The ability of an adenovirus vector design to minimize the potential for RCA generation can be assessed by determining the RCA level in a cycle of vector production using a bioassay. The assay scores for RCA generated during vector production by using cell lines that are not permissive for replication-incompetent deletion vectors and will only support the growth of wild-type adenovirus. These cell lines are infected with a vector stock, and the presence or absence of an observable cytopathic effect (CPE) is used to score for any generation of RCA.

Where an adenovirus deletion vector which is replication-incompetent has been packaged in a cell line that contains adenovirus sequences supplying essential viral proteins in trans, RCA generated from a recombination event contains a mixture of viral DNA sequences from both sources. Such a hybrid genome in the RCA may be characterized when the viral sequences in the cell line and the vector are derived from different virus serotypes. In this manner, the sequence heterogeneity among virus serotypes may be used to identify a recombination event by any number of techniques known to those skilled in the art, such as restriction enzyme analysis or direct DNA sequencing. Comparison of sequenced regions in the RCA to the known sequence of the adenovirus serotypes allows for identification of the source of the sequences tested. Thus, the recombination event giving rise to the RCA can be dissected by sequence analysis.

A specific example of using RCA genome analysis to identify the nature of the recombination event can be shown using adenovirus vectors deleted for the E1 region and in which the gene of interest is cloned into the E1 site. These vectors are produced in 293 cells. Where the vector is produced from an adenovirus serotype that is different than that used to construct the 293 cell line, e.g., adenovirus 2, any RCA that is generated by recombination between the adenovirus 5 sequences in the cell and the adenovirus 2 sequences in the vector can be characterized by different restriction enzyme patterns between the 2 serotypes. Furthermore, DNA sequencing can be used to identify specific sequence variations. When E1-deletion vectors are used, any RCA generated from a recombination event will incorporate the E1 region from the adenovirus 5 insert in the 293 cells, and the presence of these sequences in the RCA can be identified by characterization of the El region. The E1 region of the RCA can be mapped by restriction enzyme analysis and/or sequenced directly to determine the origin of this sequence. Therefore, the skilled artisan can confirm that the RCA contains a mixture of adenovirus 2 and adenovirus 5 sequences, indicating that a recombination event occurred between the cell and vector viral DNA sequences.

While vectors deleted for protein IX have particular relevance to the prevention of RCA during vector production in packaging cell lines that contain protein IX sequences—i.e., 293 cells—it may be understood by those skilled in the art that the concept of using gene or sequence deletion may be analogously extended to the design of vectors that minimize or delete any regions of viral sequences when used in cell lines that contain homologous viral sequences and therefore have the potential to generate RCA.

Parameters Of The Vectors

The adenovirus vectors of the invention may be derived from the genome of various adenovirus serotypes, including but not limited to, adenovirus 2, 4, 5, and 7, and in general, non-oncogenic serotypes.

The adenovirus vectors of the invention may be engineered to carry any heterologous gene for delivery and expression to a target cell. The gene may be engineered into various sites within the vectors, including but not limited to, the E1 region, the E2 region, the E3 region and the E4 region, using techniques that are well known to those skilled in the art (*Current Protocols in Molecular Biology*, Ausubel, F. et al., eds., Wiley and Sons, New York, 1995). The heterologous gene cloned into the adenovirus vector may be engineered as a complete transcriptional unit, including a suitable promoter and polyadenylation signal. Such promoters including the adenovirus E1 promoter or E4 promoter, for example, as well as others including, but not limited to, the CMV promoter and the PGK promoter. Suitable polyadenylation signals at the 3' end of the heterologous gene include, but are not limited to, the BGH and SV4O polyadenylation signals. The E3 region of the adenovirus genome may be deleted in order to increase the cloning capacity of a vector, or it may be left in the vector construct, according to conditions encountered by one practicing the present invention. It is presently preferred to leave at least a substantial portion of the E3 region in the vector so as to minimize, in some aspects, immune response by the patient to the vector construct, including serious inflammatory consequences.

Genes that may be engineered into the adenovirus vectors of the invention include, but are not limited to, CFTR for CF, α1-antitrypsin for emphysema, soluble CD4 for AIDS, ADA for adenosine deaminase deficiency and any other genes that are recognized in the art as being useful for gene therapy.

The vectors of the present invention may have application in gene therapy for the treatment of diseases which require that a gene be transferred to recipient cells for the purpose of correcting a missing or defective gene, or for the purpose of providing a therapeutic molecule for treatment of a clinical condition.

The vectors of the present invention can be adapted to ex vivo and in vitro gene therapy applications.

It will be understood that the concepts of vector designs contained in the foregoing sections may analogously be applied to other viral vectors, including, but not limited to, retrovirus, herpes, adeno-associated virus, papovavirus, vaccinia, and other DNA and RNA viruses.

EXAMPLE 1

Figure 3:
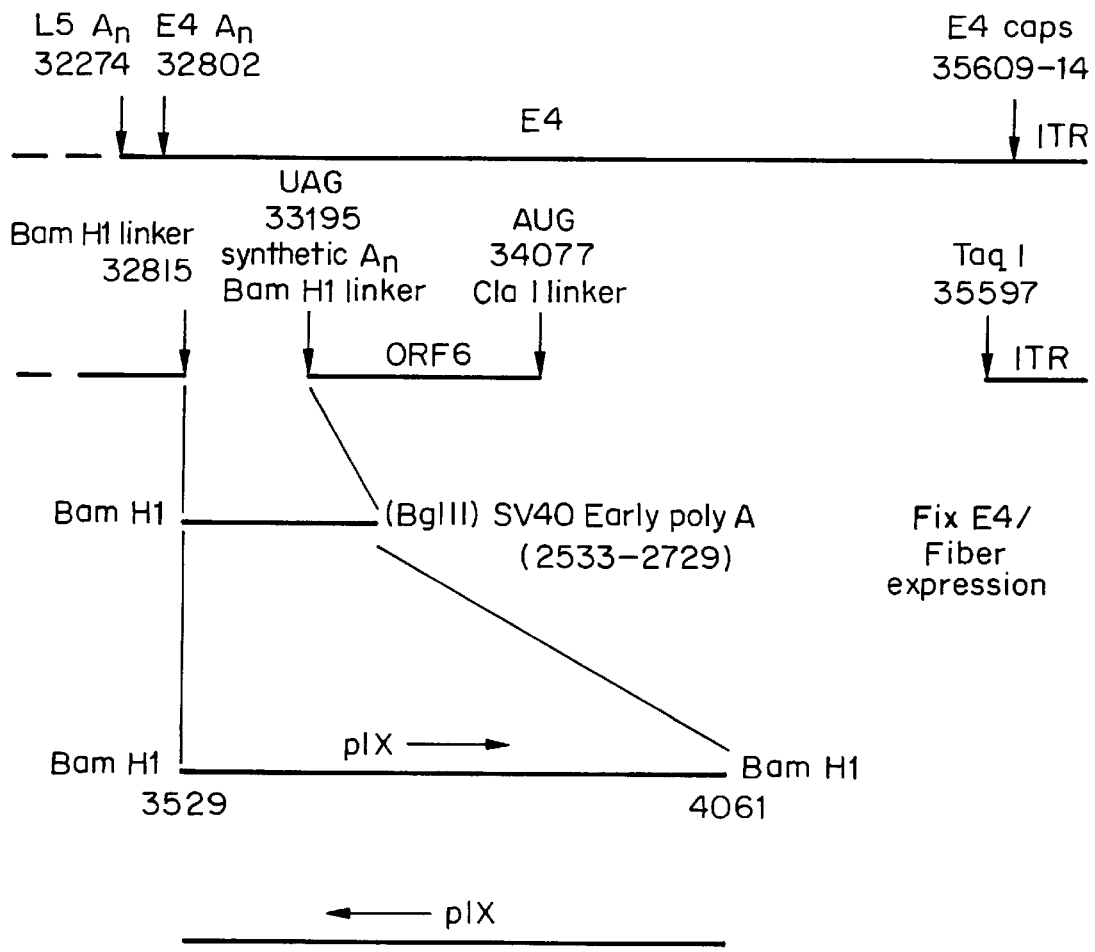
FIG. 3 The 3' end of a novel vector is depicted, in which protein IX is repositioned to the E4-deleted region so as to minimize recombination between a vector and 293 cells.

Construction of a Scrambled Adenovirus Vector that Prevents Protein IX-Dependent Recombination A novel adenovirus vector is constructed by starting with the plasmid Ad2E4ORF6 (PCT Publication Number WO 94/12649), deleted for E1 and in which E4 sequences are deleted from the ClaI site at 34077 to the TaqI site at 35597. The ORF6 sequence from 33178 to 34082 is inserted into the E4 region. The SV4O early polyA sequence is inserted adjacent to the ORF6, which also serves to prevent readthrough from the ORF6 gene into the L5 (fiber) sequences. Protein IX is repositioned from its original location in the virus genome into the E4-deleted region as a Bam HI fragment. The protein IX fragment contains its own promoter, and may be cloned into the vector in either direction. The construct is shown in FIG. 3. The plasmid is transfected into 293 packaging cells to produce a vector stock using standard techniques (*Current Protocols in Molecular Biology*, Ausubel, F., et al., eds., Wiley & Sons, 1995). The resulting vector is less susceptible to a recombination event with viral sequences in 293 cells due to the repositioning of the protein IX gene, which decreases homology between the vector and the 293 cell.

Figure 4:
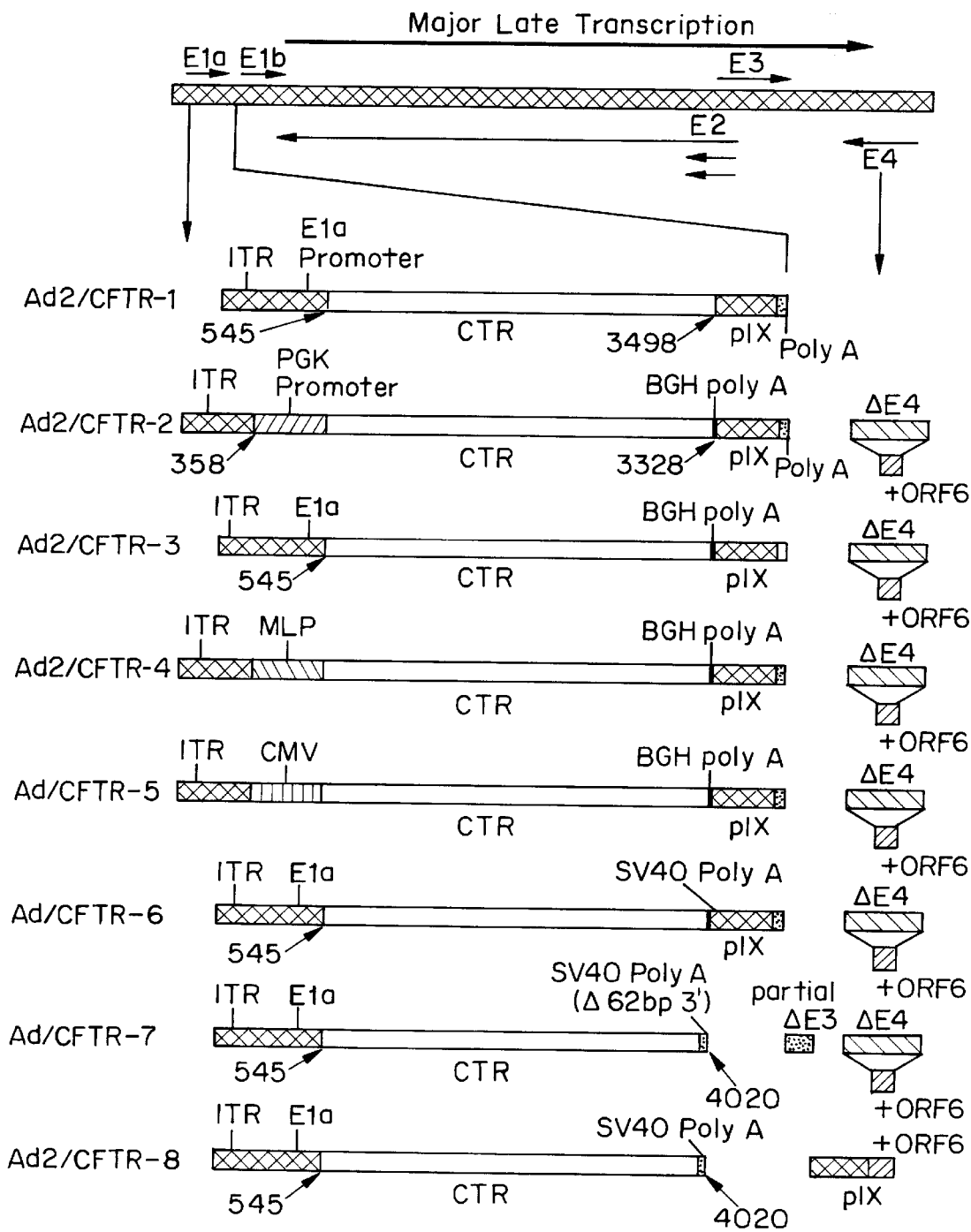
FIG. 4 Schematic diagram of various adenovirus vectors deleted for the E1 region and containing the CFTR gene cloned into the E1 site in the adenovirus genome. The CFTR gene is under the control of a specific eucaryotic transcriptional promoter and polyA site as illustrated in each vector. Additional alterations of the adenovirus genome in each vector are shown.
Figure 6:
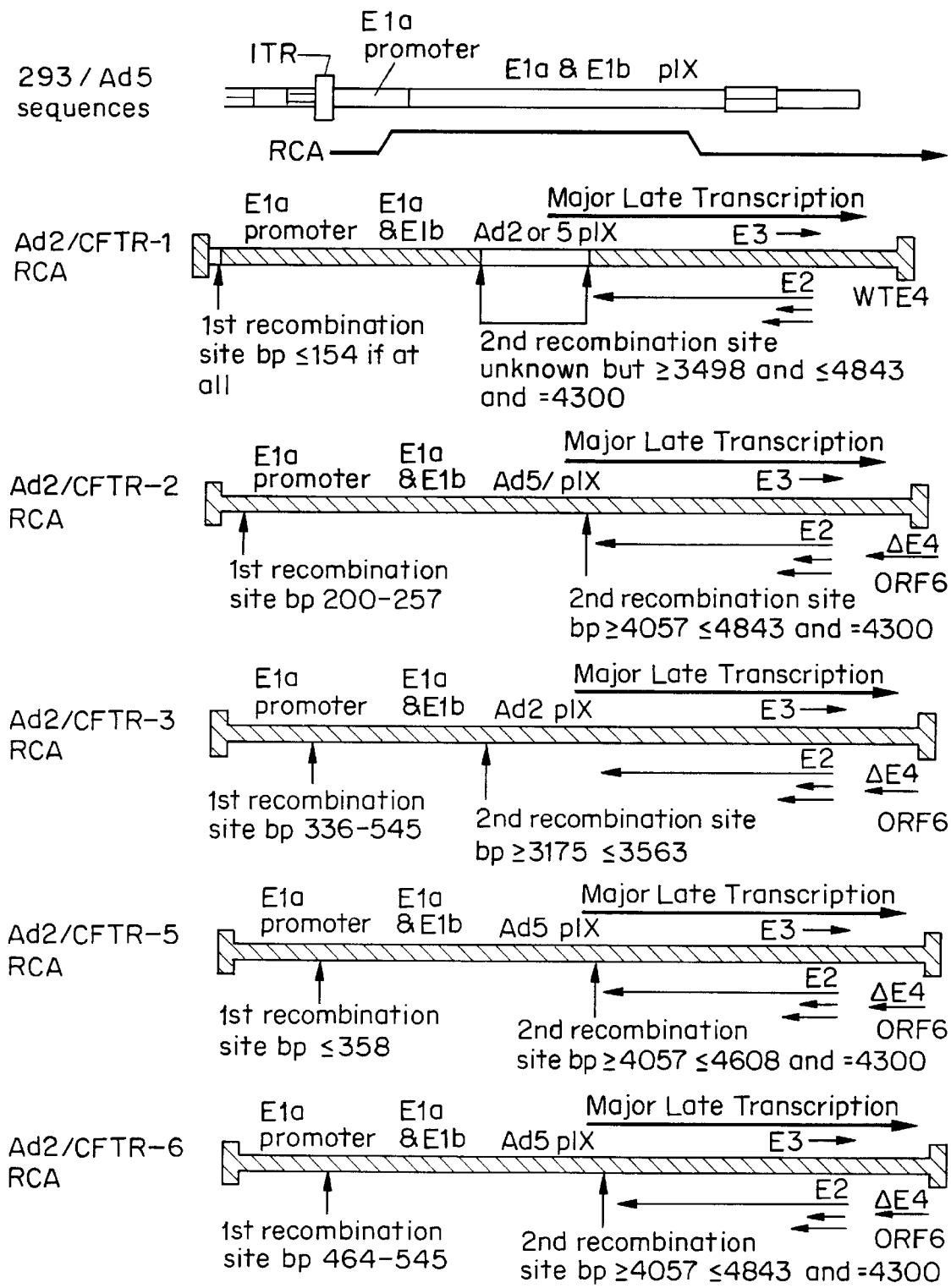
FIG. 6 Schematic diagram of RCA generated during vector production in 293 cells. The structure of RCA is shown with reference to the specific nucleotide borders of the recombination site and to the serotype source of the E1 region and the protein IX gene.

Ad2/CFTR-8 is an example of an adenovirus vector in which protein IX has been repositioned into the E4 region of the virus genome, and is shown in FIG. 4.

EXAMPLE 2

Analysis of RCA by Serotype Sequence Heterogeneity

The generation of RCA arising from recombination between an adenovirus vector and 293 cells was analyzed by sequence analysis of replication-competent virus that arose during vector production. The vectors were derived from adenovirus serotype 2 and were deleted for the E1 region, but contained the protein IX sequence. The 293 cells contain the E1 region and the protein IX sequence from adenovirus serotype 5. Sequence heterogeneity between adenovirus serotypes 2 and 5 was used to identify the source of E1 and protein IX sequences that were contained in the RCA. If the protein IX sequence in the RCA is derived from adenovirus 5, then a homologous recombination event between the vector and the 293 cells can be scored. Sequence heterogeneity between these adenovirus serotypes from nucleotide 1–600 (Adenovirus type 2: SEQ ID NO:1 and Adenovirus type 5: SEQ ID NO :3) and 3041–4847 (Adenovirus type 2: SEQ ID NO :2 and Adenovirus type 5: SEQ ID NO :4).

The vectors analyzed for RCA generation during production are shown in FIG. 4. FIG. 5 shows the results of BclI restriction enzyme analysis of each vector and of the RCA generated during vector production in 293 cells. By reference to the restriction sites in the wild-type adenovirus 2 and 5 serotypes, the RCA can be characterized with respect to the source of its sequences. In such a manner, the recombination event between a vector and a packaging cell line that gives rise to RCA may be identified. FIG. 7 provides a schematic diagram of the sequence analysis of the RCA generated during production of each vector in 293 cells. The adenovirus 5 sequences contained in 293 cells, which appear at the top of each schematic, are potentially available for a recombination event with the protein IX sequence in the vector. The figure shows the recombination sites at the 5' and 3' ends of the E1 insert in the RCA for each vector tested. In RCA generated during production of vectors Ad2/CFTR-2, Ad2/CFTR-5 and Ad2/CFTR-6, the protein IX sequence at the 3' boundary of the E1 fragment in the RCA is derived from adenovirus 5, indicating that a recombination event occurred between the vector and the 293 cells, mediated by the protein IX sequence. The results from Ad2/CFTR-3 and Ad2/CFTR-1 were variable, and recombination that was not mediated by protein IX was detected.

The results of the recombination analysis of the RCA demonstrates that the protein IX sequence in an adenovirus vector can serve as a recombinogenic site for the generation of RCA in a cell line that contains a homologous protein IX sequence.

EXAMPLE 3

Construction and Analysis of Ad2/CFTR-7

A series of cloning steps was required to construct the plasmids intermediate to the final construction of vector Ad2/CFTR-7. The in vivo recombination steps to derive Ad2/CFTR-7 are detailed below. An RCA assay was used to determine whether the Ad2/CFTR-7 vector design reduced RCA generation during passage in 293 cells.

Construction of pAd2/E1aCFTRsvdra-

Figure 7A:
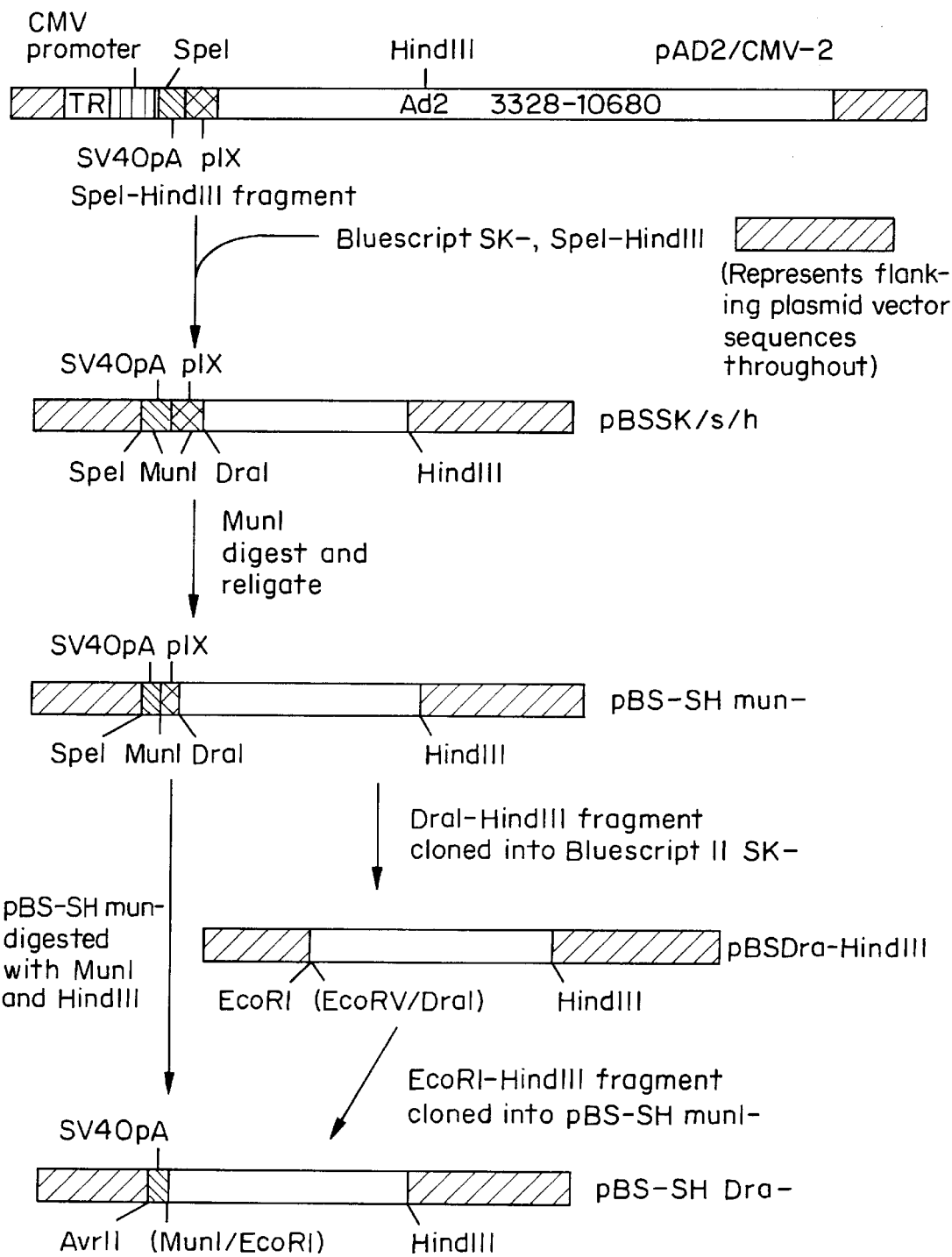
FIGS. 7A–B Schematic diagram of the construction of pAd2/E1ACFTRsvdra-.
Figure 7B:
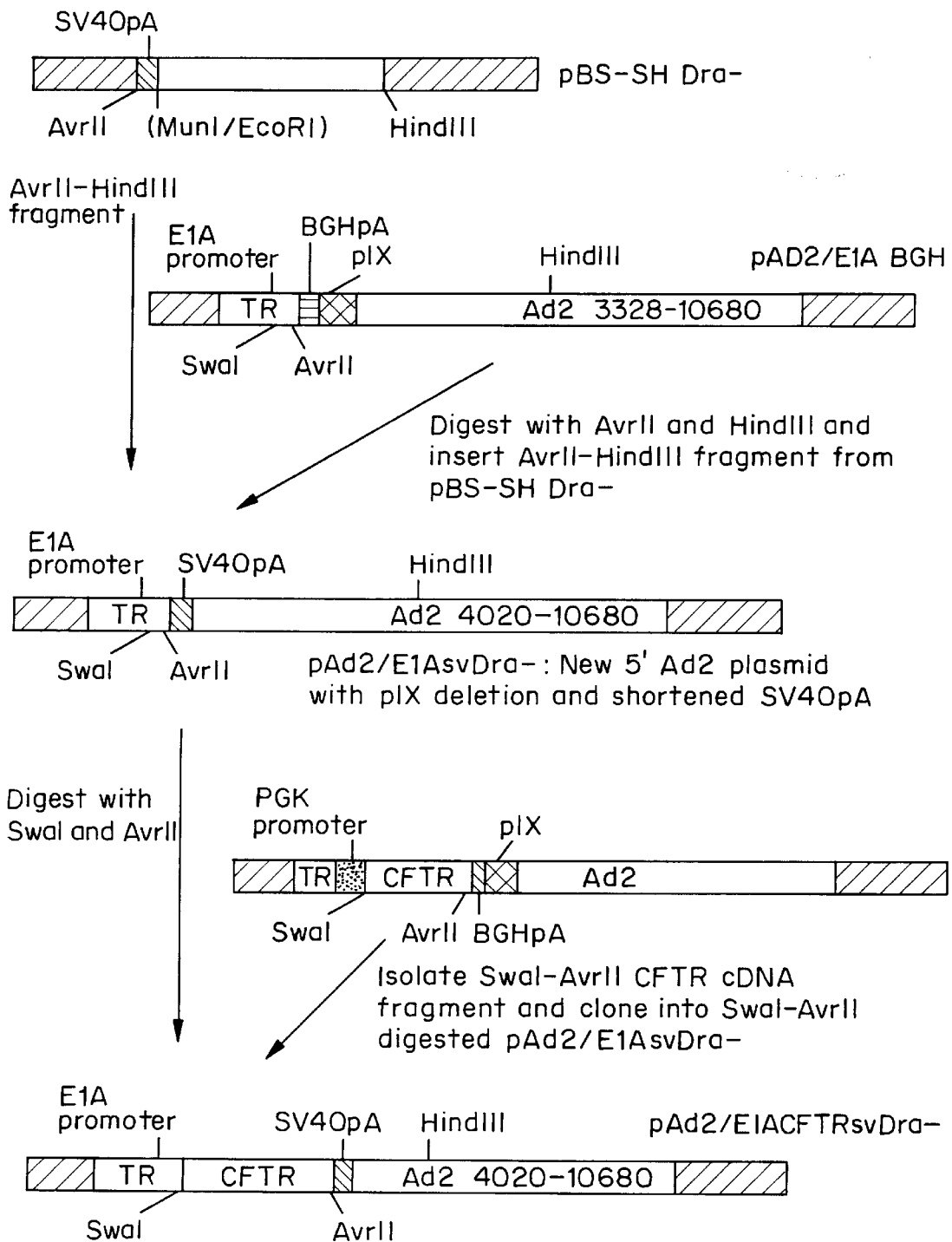

The cloning steps and plasmids used in constructing the intermediate plasmid pAd2/E1aCFTRsvdra- are described below are illustrated in FIGS. 7A and 7B. The starting plasmid, pAd2/CMV-2, contains an insert of approximately 7.5 kb cloned into the ClaI and BamHI sites of pBR322 which comprises the first 10,680 nucleotides of Ad2, except for a deletion of sequences between nucleotides 357 and 3498. This deletion eliminates the E1 promoter, E1a and most of E1b coding region. Plasmid pAd2/CMV-2 also contains a CMV promoter inserted into the ClaI and SpeI sites at the site of the E1 deletion and a downstream SV4O polyadenylation (polyA) sequence (originally a 197 bp BamHIBclI fragment) cloned into the BamHI site.

The first series of cloning steps first deleted a portion of the SV4O polyA and a portion of the protein IX gene and subsequently the remainder of the protein IX gene. Plasmid pAd2/CMV-2 was digested with SpeI and HindIII. The 3146 bp fragment containing the SV4O polyA and Ad2 sequences was ligated into the same sites of pBluescript SK— (Stratagene) to produce plasmid pBSSK/s/h. The 656 bp MunI fragment containing 60 nucleotides of the SV4O polyA and the majority of the protein IX sequences of Ad2 was excised from this plasmid to produce plasmid PBS-SH mun-. This plasmid was digested with DraI and HindIII and the 2210 bp fragment was cloned into the EcoRV and HindIII sites of pBluescript SKII—(Stratagene) resulting in plasmid pBSDra-HindIII. In this step, the remainder of the protein IX gene was removed. The EcoRI—HindIII fragment (2214 bp) of this plasmid was then cloned into the MunI and HindIII sites of plasmid pBS-SHmun- producing pBS-SH.dra-. In this step, the segment of the Ad2 genome with the protein IX deletion is rejoined with the truncated SV4O polyA segment. Plasmid pBS-SH.dra- thus has a 60 bp deletion of SV4O polyA, a deletion of the protein IX gene, and Ad2 sequences from bp 4020 through 10680. This insert is also surrounded by polylinker sites.

In the next series of cloning steps, the DNA segment produced above containing the SV4O polyA and the protein IX deletion was joined with sequences required to complete the left end of the Ad2 genome. pBS-SH.dra- was digested with AvrII and HindIII and the 2368 bp fragment was cloned into the AvrII and HindIII sites of plasmid pAdElaBGH, effectively replacing the BGH polyA, protein IX and Ad2 sequences from this plasmid and thus producing plasmid pAd2/E1asvdra-.

In the next series of cloning steps, the CFTR CDNA was introduced downstream from the E1A promoter in pAd2/E1asvdra-. To accomplish this a SwaI and AvrII fragment containing the CFTR CDNA was released from plasmid pAdPGKCFTRsv and inserted into the SwaI and AvrII sites of pAd2/Elasvdra- to produce plasmid pAd2/E1aCFTRsvdra-. This plasmid was used in the in vivo recombination described below.

Construction of pAd2/ORF6EΔ1.6

Figure 8:
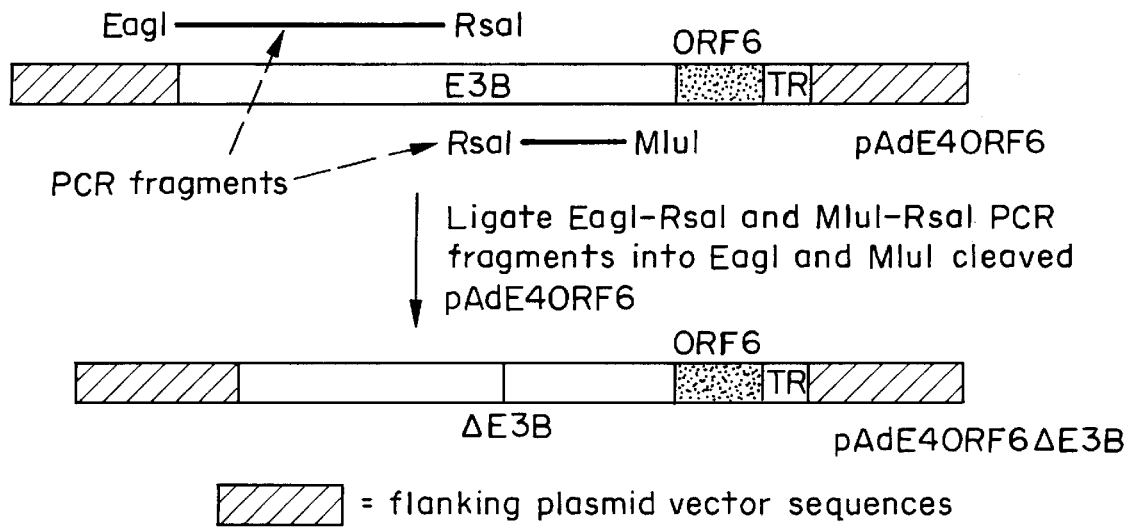
FIG. 8 Schematic diagram of the construction of pAdE4ORF6ΔE3B.
Figure 9:
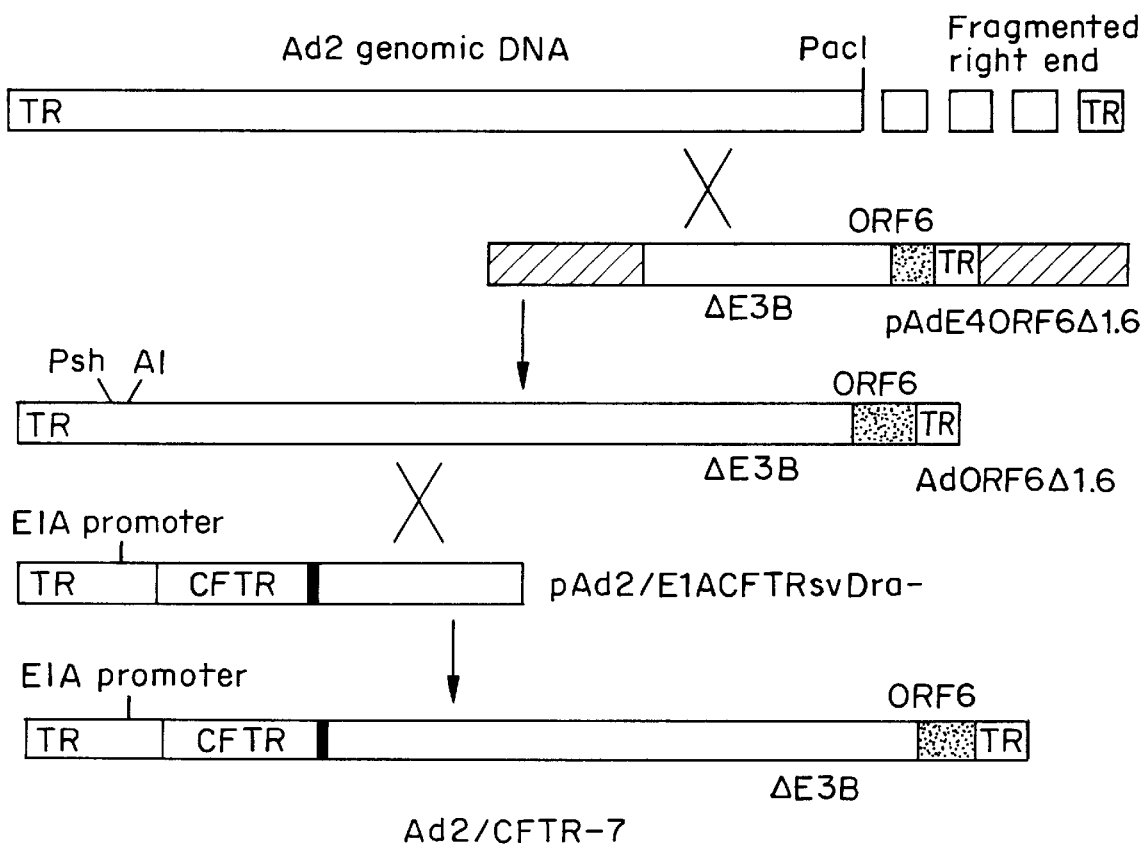
FIG. 9 Schematic diagram of in vivo recombination steps used to produce Ad2/CFTR-7.

The cloning steps and plasmids for preparing pAD2/ORF6EΔ1.6 are detailed in FIG. 8. The starting plasmid, pAdE4ORF6, was described in PCT Publication Number WO 94/12649. The 1.6 kb deletion within the E3 region of this plasmid was constructed by three-way ligation of two PCR fragments into MluI and EagI cut pAdE4ORF6. The PCR fragments were both made using pAdE4ORF6 DNA and the first PCR fragment corresponded to Ad2 nucleotides 27123 through 29292 (2169 bp) and was flanked by EagI and RsrII sites respectively. The second PCR fragment corresponded to Ad2 nucleotides 30841 through 31176 (339 bp) and was flanked by RsrII and MluI sites respectively. When ligated with MluI and EagI cut pAdE4ORF6 DNA the resulting plasmid pAdORF6Δ1.6 contained a deletion of Ad2 nucleotides 29293 through 30840 (1547 bp) or all of E3b except for the polyA site. It retained the rest of the Ad2 sequences from 27123 through 35937 and also now contains a unique RsrII site.

In vivo Recombination Steps Used to Derive Ad2/CFTR-7

Figure 10:
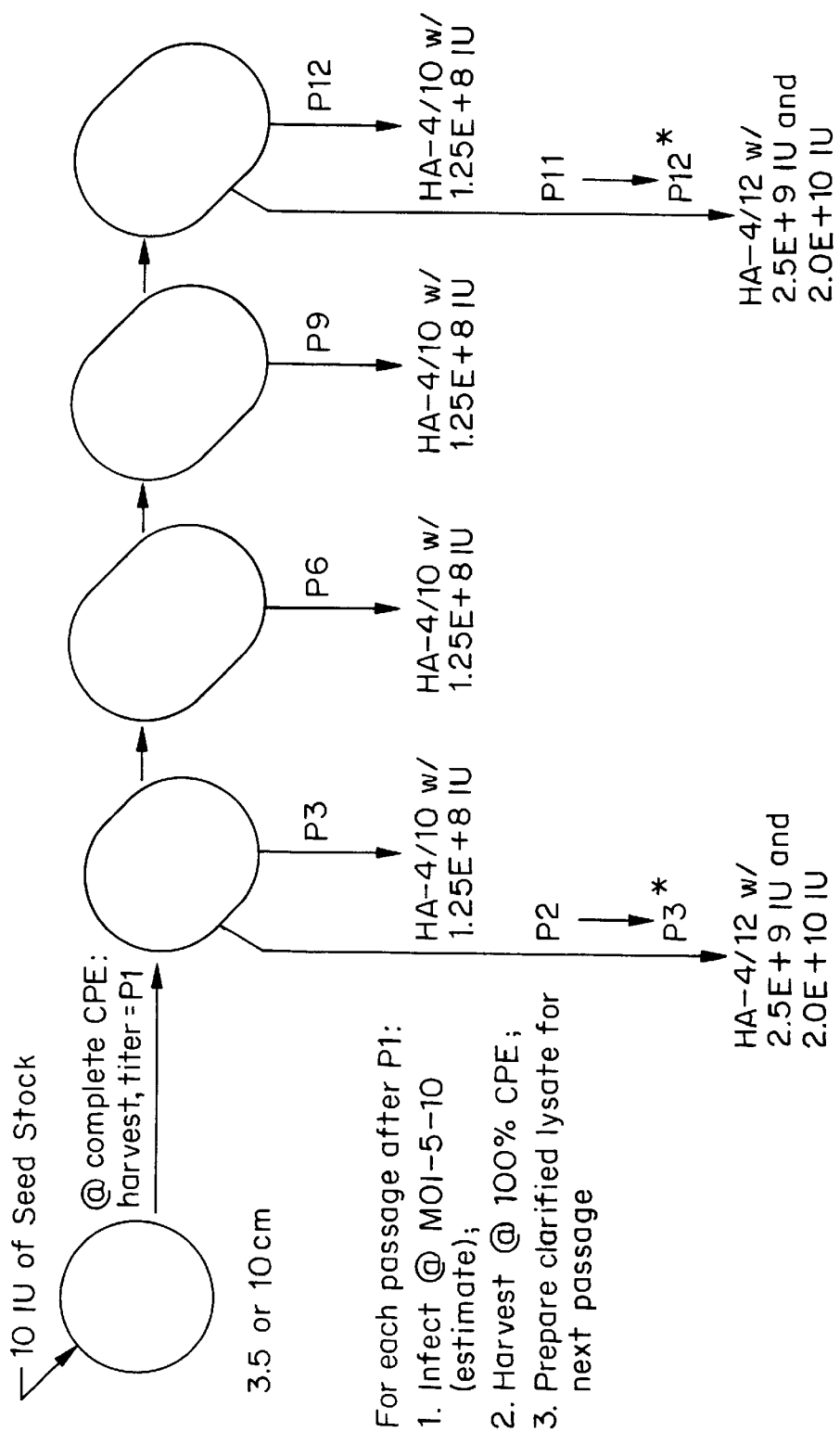
FIG. 10 Schematic diagram of experiments to assay RCA generation during multiple passages of adenovirus vectors in 293 cells. The schedule of passages is shown along with the RCA bioassay performed after passages 3, 6, 9 and 12. HA refers to the HeLa and A549 cells used sequentially in the assay; the 2 numbers following indicate the number of days, respectively, of infection in each cell line.

The recombination steps used to derive the DNA construct of Ad2/CFTR-7 are illustrated in FIG. 10.

Plasmid pAd2E4ORF6Δ1.6 linearized with ClaI (polylinker region of plasmid past Ad2 bp 35937) and Ad2 DNA digested with PacI (bp 28622 of Ad2) and AseI (multiple cuts 3' of PacI) were introduced into 293 cells using CaPO$_4$ transfection. The desired recombinant virus resulting from this step, AdORF6Δ1.6, was plaque purified and used to produce a seed stock. Next, pAd2/E1aCFTRsvdra- was cleaved with BstBI at the site corresponding to the unique BstBI site at 10670 in Ad2. Genomic DNA from Ad2/ORF6E3Δ1.6 was digested with PshAI which cleaves twice in the 5' region of the virus. Plasmid and genomic DNAs were then transfected with CaPO$_4$ (Promega) into 293 cells. The desired recombinant vector resulting from this step, Ad2/CFTR-7, was plaque purified and used to produce a seed stock. Ad2/CFTR-7 is shown in FIG. 4.

EXAMPLE 4

RCA Assay of Vectors Passage in 293 Cells

The Ad2/CFTR-7 vector was tested to determine if RCA generation arose during blind passages when compared with other vectors in which the protein IX region is retained. An RCA bioassay was used to score for RCA. A schematic diagram of the RCA assay design is shown in FIG. 10.

A schematic diagram of the vectors tested is shown in FIG. 4. The vectors tested in comparison to Ad2/CFTR-7 include Ad2/CFTR-1, Ad2/CFTR-2, and Ad2/CFTR-6. All of these control vectors contain the protein IX gene.

A seed stock of each vector was prepared by growth of the virus in 293 cells, which contain the adenovirus E1 region and are permissive for the replication of E1-deletion vectors. The seed stock was titered on 293 cells.

Serial passaging of the seed stock was performed on 293 cells. An inoculum of virus at an M.O.I. (multiplicity of infection) of 5–10 was used to infect the cells. Each passage was harvested when the cytopathic effect (CPE) was observed to be 100%, and a lysate was prepared according to standard techniques.

The assay of RCA generation in 293 cells was tested by a bioassay for replication competent virus which was performed using HeLa cells and A549 cells. These cell lines do not contain any adenovirus E1 sequences, and are therefore only permissive for viruses which contain the E1 region by design or have acquired it by a recombination event. Therefore, the assay scores for any RCA generated from a recombination event between an E1-deleted vector and the 293 cells.

Selected passages of each vector through 293 cells were analyzed by the RCA assay. The assay was performed by infecting HeLa cells with the vector passage to be tested at an MOI of 20. This infection was allowed to proceed for 4 days, after which the cells were harvested and a lysate prepared by standard techniques. The lysate was then used to infect A549 cells, and this infection proceeded for 10 days. The cells were scored for the presence or absence of CPE. Table 1 sets forth the results of RCA assays performed on selected passages of each vector tested. A passage was scored as PASS if no RCA was observed, and was scored as a FAIL if RCA was observed, as determined by any observation of CPE. The dose of vector tested in the RCA assay was varied, as shown.

The results from the RCA assay show that RCA was observable in passage 12 from vectors Ad2/CFTR-2 and Ad2/CFTR-6, and in passage 3 from vector Ad2/CFTR-1. In contrast, no RCA was observed at passage 12 from vector Ad2/CFTR-7, even at the highest dose tested. This vector has the lowest levels of RCA of the vectors tested. The results indicate that removal of the protein IX sequences has significantly reduced RCA generation in 293 cells.

TABLE 1

| Adenovirus Vector | Seed Stock Titer (IU/ml) | Passage Titers (IU/ml) | Dose Tested in RCA Assay | | |
|---|---|---|---|---|---|
| | | | $1.25 \times 10^8$ IU | $2.5 \times 10^9$ IU | $2.0 \times 10^{10}$ IU |
| Ad2/CFTR-1 | $1.0 \times 10^8$ | P1: $2.2 \times 10^9$<br>P6: $3.6 \times 10^9$ | P3, P6, P9, P12: PASS | P3: PASS<br>P12: PASS | P3: FAIL<br>P12: PASS |
| Ad2/CFTR-2 | $3.8 \times 10^8$ | P1: $7.2 \times 10^9$<br>P6: $2.2 \times 10^9$ | P3, P6, P9, P12: PASS | P3: PASS<br>P12: FAIL w/4 | P3: PASS<br>P12: FAIL 100% |
| Ad2/CFTR-6 | $7.6 \times 10^8$ | P1: $1.8 \times 10^9$<br>P7: $3.0 \times 10^9$ | P3, P6, P9, P12: PASS | P3: PASS<br>P12: PASS | P3: PASS<br>P12: FAIL w/20 |
| Ad2/CFTR-7 | $1.1 \times 10^8$ | P1: $3.4 \times 10^7$<br>P7: $1.9 \times 10^8$ | P3, P6, P9, P12: PASS | P3: PASS<br>P12: PASS | P3: PASS<br>P12: PASS |

Results of the RCA assay performed on selected passages of each vector through 293 cells are shown. The seed stock titer and passage titers were performed on 293 cells. The RCA assay was performed as described in EXAMPLE 3. The observation of CPE in the assay was scored as a FAIL, while the absence of CPE was scored as a PASS.

EXAMPLE 5

Adenovirus Vectors with Minimal E4 Sequence

Plasmid pAdE4ORF6 was described in PCT Publication Number WO 04/12649 and used to construct Ad2-ORF6/PGK-CFTR, also described in the same publication. It contains the CFTR gene under the control of the PGK promoter. Ad2/CFTR8, shown in FIG. 5, is an adenovirus vector which is equivalent to Ad2-ORF6/PGK-CFTR.

Further modifications of this vector design are an aspect of the present invention. The CFTR gene may alternatively be placed under the control of the CMV promoter, as illustrated by Ad2/CFTR-5, as shown in FIG. 5. Other promoters which can be used include the adenovirus major late promoter (MLP), as illustrated in the vector Ad2/CFTR-4. The BGH and SV4O polyA elements can be used in vector construction, as well as others known to those skilled in the art.

We claim:

1. A replication-defective adenovirus vector having a deleted E1 region of the adenovirus genome, and in which the protein IX gene has been relocated in the adenovirus genome to a location thereof other than the location in which said protein IX gene normally resides, such that generation of replication-competent adenoviruses is minimized or eliminated.

2. The vector of claim 1 in which one or more open reading frames of the E4 region is deleted.

3. The vector of claim 2, in which the protein IX gene is relocated to the E4 region.

4. The vector of claim 2, in which ORF6 of the E4 region is retained.

5. The vector of claim 4, in which the protein IX gene is inserted adjacent to the ORF6 gene.

6. The vector of claim 1, in which the adenovirus is selected from among adenovirus serotypes 2, 4, 5 and 7.

* * * * *